`United States Patent` [19]

Hofmeister et al.

[11] 4,102,908

[45] Jul. 25, 1978

[54] PROCESS FOR THE PREPARATION OF PREGNANE DERIVATIVES

[75] Inventors: Helmut Hofmeister; Klaus Annen; Henry Laurent; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 802,329

[22] Filed: Jun. 1, 1977

[30] Foreign Application Priority Data

Jun. 2, 1976 [DE] Fed. Rep. of Germany ....... 2625306

[51] Int. Cl.² ............................................. C07J 5/00
[52] U.S. Cl. ................................................ 260/397.4
[58] Field of Search ..................................... 260/397.4

[56] References Cited

U.S. PATENT DOCUMENTS 3,741,997  6/1973  Berndt et al. ..................... 260/397.4
3,764,615  10/1973  Hauser ............................... 260/397.4

OTHER PUBLICATIONS

"Organic Reactions in Steroid Chemistry" by Fried et al. (1972).

Primary Examiner—Elbert L. Roberts
Attorney, Agent, or Firm—Millen & White

[57] ABSTRACT

A process for the preparation of pregnane derivatives of the formula

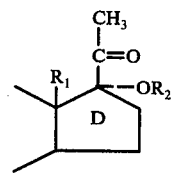

wherein $R_1$ is methyl or ethyl and $R_2$ is methyl, ethyl, formyl, or acetyl, comprises reacting a nitrate ester of the formula

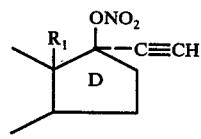

wherein $R_1$ is as above, in the presence of a catalytic amount of a mercury salt of a lower carboxylic acid with formic acid or acetic acid in a dipolar aprotic or basic solvent or with methanol or ethanol in an aprotonic, especially water-miscible, solvent in the presence of a mineral acid.

8 Claims, No Drawings

PROCESS FOR THE PREPARATION OF PREGNANE DERIVATIVES

BACKGROUND OF THE INVENTION

This invention relates to a method for building up pregnane side chains in steroids. Reported methods, e.g., those reported in J. Amer. Chem. Soc., vol. 89 (1967): 5505, and J. Org. Chem., vol. 33 (1968): 3294, are useless for commercial scale manufacture of pregnane derivatives, both because too many reaction steps are required to build up the pregnane side chain and because individual reaction steps are too expensive for a commercially feasible process.

A process for the preparation of 17α-acyloxy- and/or 17α-alkoxy-20-ketopregnane derivatives from 17α-ethynylgonane-17β-sulfite esters using mercury salts is recited in DOS's (German Unexamined Laid-Open Applications) U.S. Pat. No. 2,023,122, now U.S. Pat. Nos. 3,741,997; and 2,140,291 and 2,230,286, both now U.S. Pat. No. 3,764,615, both incorporated herein by reference.

However, this process is readily usable only on a laboratory scale, because of limitations on the yields attainable.

SUMMARY OF THE INVENTION

This invention relates to a process for the conversion of a 17α-ethynyl-17β-hydroxy steroid to a 17-methyl or ethyl ether or 17-formyl or acetyl ester of a 17α-hydroxy-17β-acetyl steroid, which comprises reacting the 17-nitrate ester of the 17α-ethynyl-17β-hydroxy steroid in the presence of a catalytic amount of a mercury salt (a) with formic acid or acetic acid in a dipolar aprotic or basic solvent to produce the 17-formate or 17-acetate ester, respectively, or (b) with methanol or ethanol in an aprotonic water-miscible solvent in the presence of a mineral acid to produce the 17-methyl or 17-ethyl ether, respectively.

DETAILED DESCRIPTION

17α-Ethynyl-17β-nitro-oxy steroids utilized as starting materials for the process for this invention can be produced from the corresponding 17β-hydroxy-17α-ethynyl steroids by reaction with acetyl nitrate, as disclosed in Fed. Rep. of Germany Application DAS 1,643,034 and Tetrahedron, vol. 25: 761 (1969), whose disclosures are incorporated by reference.

The 17α-ethynyl-17β-nitro-oxy steriod starting material can be substituted in the usual manner, including as substituents etherified and esterified hydroxy in the 1-, 3-, 6-, or 11-positions; keto in the 3- or 11-positions; fluorine in the 6- or 9-positions; methyl in the 1-, 2-, 4-, or 6-positions; or methylene in the 1α,2α-, 5β,10β-, or 6α,7α- and 6,7β-positions. Starting compounds can have an aromatic A-ring or have double bonds, for example in the 1-, 3-, 4-, 5(6)-, 5(10)-, 6-, or 9(11)-positions.

The process of this invention is preferably utilized within the scope of total steroid synthesis, preferred starting compounds being 17α-ethynyl-17α-nitrate esters which, in turn, can be produced by total synthesis. Esters particularly preferred as starting materials are nitrate esters of Formula III

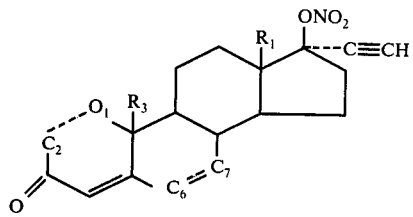

wherein $R_1$ is methyl or ethyl, $R_3$ is hydrogen or methyl, and $C_1$═$C_2$ and $C_6$═$C_7$ are C—C single or C═C double bonds.

To conduct the process of this invention, a 17α-ethynyl-17β-nitrate ester is reacted in the presence of a catalytic amount of a mercury salt in a suitable solvent, with a reagent of the formula $R_2OH$ wherein $R_2$ is formyl, acetyl, methyl, or ethyl.

When $R_2$ is formyl or acetyl, a dipolar aprotic or basic solvent is utilized for this purpose. Examples of dipolar aprotic solvents are hexamethylphosphoric triamide, dimethylformamide, dimethylacetamide, dimethyl sulfoxide, and sulfolane, of which hexamethylphosphoric triamide is preferred. Examples of basic solvents are pyridine, toluidine, N-methylpyrrolidone, and triethylamine.

When $R_2$ is methyl or ethyl, aprotonic solvents, especially those which are miscible with water, are utilized in the presence of a mineral acid.

Examples of suitable solvents are tetrahydrofuran, dioxane, and acetone, of which tetrahydrofuran is preferred. Particularly preferred mineral acids are sulfuric acid, nitric acid, and perchloric acid.

Mercury salts usable as catalyst include all readily dissociated mercury(I) and mercury(II) salts, for example, salts of organic or inorganic acids, preferably of of acids having a dissociation constant of at least e.g., mercury(I) and mercury(II) acetate, mercury(I) and mercury(II) nitrate, mercury sulfate, mercury(I) and mercury(II) trifluoroacetate, and mercury formate. The mercury salt is added in catalytic amounts, e.g., about 5 to 25 Mol%, preferably about 10 to 15 Mol%, calculated on the starting steroid. However, larger quanties do not adversely affect the reaction.

In the process for the preparation 17-formyloxy or 17-acetoxy compounds, the mercury salt is preferably of a lower carboxylic acid, most preferably mercury(I) or (II) formate, acetate or trifluoroacetate.

In the process for preparing the 17-methoxy or 17-ethoxy compounds, mercury(I) or (II) formate, acetate, trifluoroacetate or nitrate is preferred.

Inert solvents can be added to the reaction mixture as diluents. Suitable inert solvents are, for example, polar aprotic solvents, such as dimethylformamide, dimethylacetamide, dimethyl sulfoxide, dioxane, and tetrahydrofuran.

The process of this invention is generally conducted at room temperature, but the reaction can be effected without difficulty at temperatures in a range from −10° to 80° C.

The results of the process of this invention are unexpected, because it could not be foreseen that 17β-nitrate esters would give high yields of desired 20-keto-17α-formate by the reaction of this invention, owing to formation of the undesired 20-keto-17β-formate as a major by-product of the conventional sulfite ester reaction. Presumably, the reaction mixture initially forms a π-complex with the mercury salt. After the electrophilic attack of the $OR_2$-group, the inversion of the carbon group occurs

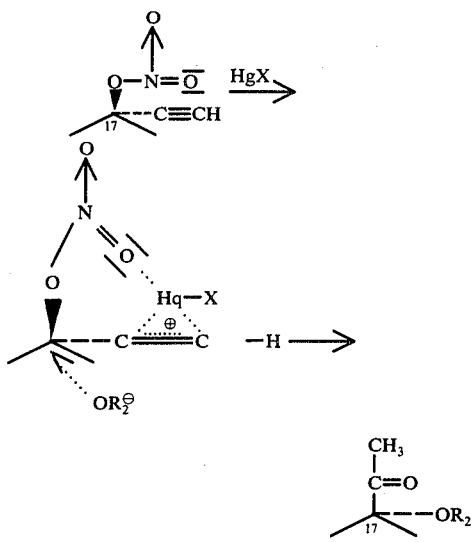

It is possible using the process of this invention to prepare pregnane derivatives of 17-oxoandrostanes and -estranes by a synthesis which can be easily conducted on a commercial scale. This process is a particularly valuable contribution toward total synthesis of pregnane compounds, e.g., progestationally active 17α-hydroxy-progesterone derivatives, such as 17α-hydroxyprogesterone caproate or 6-chloro-17α-acetoxy-4,6-pregnadiene-3,20-dione; and anti-inflammatorily active corticoids, such as hydrocortisone, prednisolone, triamcinolone, and dexamethasone, and the corresponding 18-methyl steroids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

PREPARATION 2.0 g. of 17β-hydroxy-17α-ethynyl-4-estren-3-one dissolved in 40 ml of chloroform is slowly dropped in a solution of 14.2 ml of acetic acid anhydride and 9.1 ml of concentrated nitric acid (d = 1.50) under cooling at −10° C. The reaction mixture is stirred during 30 minutes, poured into ice water and extracted with methylene chloride. The extract is washed with an aqueous solution of sodiumhydrogencarbonate and with water until neutral, dried and concentrated under vacuum. By addition of 10,0- 11,5% acetone/pentane to a solution of aceton/hexane 478 mg of 17β-nitro-17α-ethynyl-4-estren-3-one is obtained (m.p. 127,5°- 129° C)

UV:$\epsilon_{239}$ = 17 600 (methanol)

EXAMPLE 1

With ice cooling and agitation, 150 g. of 17α-ethynyl-17β-nitro-oxy-4-estren-3-one in 1.75 l. of concentrated formic acid is combined with 250 ml. of hexamethylphosphoric triamide. After adding 17.5 g. of mercury(II) acetate, the mixture is stirred at room temperature, with temperature control. If the solution heats up to a greater extent after one-half to 1 hour, the mixture is cooled with water for a short time. After 5 hours, the solution is stirred into ice/water. The thus-precipitated product is vacuum-filtered, washed with water, taken up in ethyl acetate, and dried over sodium sulfate. After chromatography of the crude product on silica gel with 11–15% acetone/hexane, the yield is 124.8 g. of 17-formyloxy-19-nor-4-pregnene-3,20-dione; m.p. 204°–206° C. (decomposition); $[\alpha]_D^{20}$ = +35° (chloroform).

EXAMPLE 2

As described in Example 1, 30.0 g. of 17α-ethynyl-17β-nitro-oxy-4-estren-3-one in 350 ml. of concentrated formic acid is combined with 50 ml. of hexamethylphosphoric triamide and 3.5 g. of mercury(I) acetate. After 12 hours, the solution is added to ice/water and worked up as described in Example 1. After chromatography of the crude product on silica gel with 11–13% acetone/hexane, 21.5 g. of 17-formyloxy-19-nor-4-pregnene-3,20-dione is obtained, m.p. 202°–204° C. (decomposition); $[\alpha]_D^{20}$ = +32.7° (chloroform).

EXAMPLE 3

3.0 g. of 17α-ethynyl-17β-nitro-oxy-4-estren-3-one is dissolved in 15 ml. of triethylamine and combined with ice cooling with 30 ml. of concentrated formic acid. To this mixture is added 600 mg. of mercury(II) trifluoroacetate and the mixture is then agitated at room temperature. After 4 hours, the reaction mixture is diluted with ethyl acetate and neutralized with sodium bicarbonate solution. The solution is dried and concentrated under vacuum. After purifying the crude product with activated carbon in acetone, the yield is 2.3 g. of 17-formyloxy-19-nor-4-pregnene-3,20-dione; m.p. 201°–203° C. (decomposition); $[\alpha]_D^{20}$ = +34° (chloroform).

EXAMPLE 4

With ice cooling and agitation, 200 g. of 17α-ethynyl-17β-nitro-oxy-4-androsten-3-one in 2.3 l. of concentrated formic acid is combined with 330 ml. of hexamethylphosphoric triamide. After the addition of 23.0 g. of mercury(II) acetate, the mixture is allowed to react with temperature control as set forth in Example 1. After 8 hours, the reaction mixture is added to ice/water and worked up as described in Example 1. After chromatography of the crude product on silica gel with 10–14% acetone/hexane, the yield is 152 g. of 17-formyloxy-4-pregnene-3,20-dione; m.p. 220°–221° C. (decomposition); $[\alpha]_D^{20}$ = +87.1° (chloroform).

EXAMPLE 5

At −20° C., 15 ml. of concentrated nitric acid is gradually added dropwise to a suspension of 20 g. of 17α-ethynyl-17β-hydroxy-18-methyl-4-estren-3-one in 150 ml. of acetic anhydride. After addition of the nitric acid, the mixture is agitated for another 30 minutes; the solution is then poured into methanol-containing ice/water. The thus-precipitated product is vacuum-filtered and dissolved in ethyl acetate. The solution is washed with water, dried, and concentrated under vacuum. After chromatography of the crude product on silica gel with 16–20% acetone/hexane, the yield is 17.6 g. of 17α-ethynyl-18-methyl-17β-nitro-oxy-4-estren-3-one in the form of an oil.

As described in Example 1, 3.0 g. of 17α-ethynyl-18-methyl-17β-nitro-oxy-4-estren-3-one is reacted in 15 ml. of hexamethylphosphoric triamide and 30 ml. of formic acid with 400 mg. of mercury(II) acetate. After 5 hours, the solution is diluted with ethyl acetate, washed until neutral with sodium bicarbonate solution and water, and dried. The crude product is chromatographed on silica gel with 14–18% acetone/hexane, thus obtaining 1.8 g. of 17-formyloxy-18-methyl-19-nor-4-pregnene-3,20-dione; m.p. 194°–195° C. (decomposition); $[\alpha]_D^{20}$ = +31.8° (chloroform).

EXAMPLE 6

With ice cooling, 1.0 g. of 17α-ethynyl-17β-nitro-oxy-4-androsten-3-one in 5 ml. of hexamethylphosphoric triamide is combined with 10 ml. of glacial acetic acid. After adding 400 mg of mercury(II) acetate, the mixture is stirred at room temperature. After 8 hours, the reaction mixture is diluted with ethyl acetate and worked up as described in Example 3. After chromatography of the crude product on silica gel with 9–12% acetone/hexane, 460 mg. of 17-acetoxy-4-pregnene-3,20-dione is obtained, m.p. 243°–245° C.; $[\alpha]_D^{20}$ = +71° (chloroform).

EXAMPLE 7

A suspension of 600 mg. of yellow mercury oxide in 10 ml. of water and 0.4 ml. of concentrated sulfuric acid is heated to 60° C. for 20 minutes. After cooling to room temperature, a solution of 2.5 g. of 17α-ethynyl-17β-nitro-oxy-4-androsten-3-one in 90 ml. of tetrahydrofuran and 35 ml. of methanol is added under agitation. After 5 hours, the solution is filtered. The filtrate is diluted with ethyl acetate, washed with water, and dried. After chromatography of the crude product on silica gel with 4–6% acetone/hexane, 1.4 g. of 17-methoxy-4-pregnene-3,20-dione is obtained; m.p. 196°–197° C.; $[\alpha]_D^{20}$ = +158.6° (chloroform).

EXAMPLE 8

Analogously to Example 7, a suspension of 300 mg. of yellow mercury oxide in 5 ml. of water and 0.2 ml. of concentrated sulfuric acid is combined with a solution of 1.0 g. of 17α-ethynyl-17β-nitro-oxy-4-estren-3-one in 15 ml. of tetrahydrofuran and 5 ml. of methanol. After 4 hours, the reaction mixture is worked up. After chromatography of the product on silica gel with 9–11% acetone/hexane, the yield is 470 mg. of 17-methoxy-19-nor-4-pregnene-3,20-dione; m.p. 151°–152° C.; $[\alpha]_D^{20}$ = +106° (chloroform).

EXAMPLE 9

At −20° C., 8 ml. of concentrated nitric acid is gradually added dropwise to a suspension of 10.0 g. of 17α-ethynyl-17β-hydroxy-1,4-androstadien-3-one in 80 ml. of acetic anhydride. After 30 minutes, the solution is poured into methanol-containing ice/water. The thus-precipitated product is vacuum-filtered and worked up as described above, thus producing 7.6 g. of crude 17α-ethynyl-17β-nitro-oxy-1,4-androstadien-3-one as on oil.

7.5 g. of 17α-ethynyl-17β-nitro-oxy-1,4-androstadien-3-one is reacted, as described in Example 1, in 70 ml. of formic acid and 15 ml. of hexamethylphosphoric triamide with 800 mg. of mercury(II) acetate. After 4 hours, the solution is introduced into ice/water and the thus-precipitated product is worked up. After chromatography of the crude product on silica gel with 13–15% acetone/hexane, 5.5 g. of 17-formyloxy-1,4-pregnadiene-3,20-dione is isolated; m.p. 201°–205° C.

EXAMPLE 10

As described above, 3.8 ml. of concentrated nitric acid is gradually added dropwise at −20° C. to a suspension of 5.0 g. of 17α-ethynyl-17β-hydroxy-1,4,6-androstatrien-3-one in 45 ml. of acetic anhydride. After 15 minutes, the solution is poured into methanol-containing ice/water and the thus-precipitated product is worked up, thus produced 3.7 g. of crude 17α-ethynyl-17β-nitro-oxy-1,4,6-androstatrien-3-one.

3.6 g. of 17α-ethynyl-17β-nitro-oxy-1,4,6-androstatrien-3-one is reacted, as described in Example 1, in a mixture of 40 ml. of formic acid and 8 ml. of hexamethylphosphoric triamide with 420 mg. of mercury(II) acetate. After 3 hours, the solution is poured into ice/water and the thus-precipitated product is worked up. Chromatography of the residue on silica gel with 15–18% acetone/hexane yields 2.3 g. of 17-formyloxy-1,4,6-pregnatriene-3,20-dione; m.p. 247°–248° C.; $[\alpha]_D^{20}$ = −20.9° (chloroform).

EXAMPLE 11

5.0 g. of 17α-ethynyl-17β-hydroxy-4,6-androstadien-3-one is reacted with concentrated nitric acid in acetic anhydride, thus producing 3.4 g. of crude 17α-ethynyl-17β-nitro-oxy-4,6-androstadien-3-one as an oily product.

3.3 g. of 17α-ethynyl-17β-nitro-oxy-4,6-androstadien-3-one is reacted analogously to Example 10 in a mixture of concentrated formic acid and hexamethylphosphoric triamide with mercury(II) acetate. After 4.5 hours, the solution is poured into ice/water. The crude product obtained after the reaction mixture has been worked up is chromatographed on silica gel with 14–18% acetone/hexane, thus producing 2.1 g. of 17-formyloxy-4,6-pregnadiene-3,20-dione; m.p. 227°–229° C.; $[\alpha]_D^{20}$ = +20° (chloroform).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the conversion of a 17α-ethynyl-17β-hydroxy steroid to a 17-methyl or ethyl ether or a 17-formyl or acetyl ester of a 17α-hydroxy-17β-acetyl steroid, the improvement which comprises reacting the 17-nitrate ester of the 17α-ethynyl-17β-hydroxy steroid in the presence of a catalytic amount of a mercury salt (a) with formic acid or acetic acid in a dipolar aprotic or basic solvent to produce the 17-formate or 17-acetate ester, respectively, or (b) with methanol or ethanol in a protonic water-miscible solvent in the presence of a mineral acid to produce the 17-methyl or 17-ethyl ether, respectively.

2. The process of claim 1, wherein the starting nitrate ester is of the formula

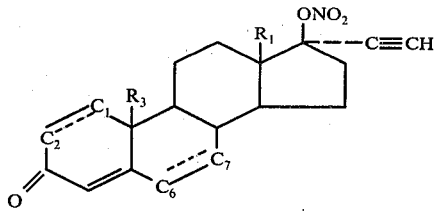

wherein $R_1$ is methyl or ethyl, $R_3$ is hydrogen or methyl, and $C_1\text{---}C_2$ and $C_6\text{---}C_7$ are C—C single or C=C double bonds.

3. The process of claim 1, wherein the mercury salt is Hg(I) or Hg(II) acetate, nitrate, trifluoroacetate, or formate.

4. The process of claim 2, wherein the mercury salt is Hg(I) or Hg(II) acetate, nitrate, trifluoroacetate, or formate.

5. The process of claim 1, wherein the 17β-nitrate ester is reacted with formic acid or acetic acid in the presence of a mercury salt of a lower carboxylic acid.

6. The process of claim 1, wherein the dipolar aprotic solvent is hexamethylphosphoric triamide.

7. The process of claim 1, wherein the protonic solvent is tetrahydrofuran.

8. The process of claim 5, wherein the dipolar aprotic solvent is hexamethylphosphoric triamide.

* * * * *